US008343351B2

(12) United States Patent  (10) Patent No.: US 8,343,351 B2
Demmer et al.  (45) Date of Patent: Jan. 1, 2013

(54) MEMBRANE FOR REMOVING PROTEASES FROM LIQUIDS

(75) Inventors: Wolfgang Demmer, Göttingen (DE); Dietmar Nussbaumer, Göttingen (DE); Hans-Heinrich Hörl, Bovenden (DE)

(73) Assignee: Sartorius AG, Gottingen (DE)

( * ) Notice: Subject to any disclaimer, the term of this patent is extended or adjusted under 35 U.S.C. 154(b) by 1101 days.

(21) Appl. No.: 11/436,861

(22) Filed: May 17, 2006

(65) Prior Publication Data

US 2006/0216807 A1  Sep. 28, 2006

Related U.S. Application Data

(62) Division of application No. 10/516,405, filed as application No. PCT/EP03/06366 on Jun. 17, 2003.

(30) Foreign Application Priority Data

Jul. 11, 2002 (DE) .................................. 102 31 574

(51) Int. Cl.
B01D 15/00 (2006.01)
(52) U.S. Cl. .......................... 210/660; 435/183; 435/212
(58) Field of Classification Search .................. 210/660; 435/183, 212
See application file for complete search history.

(56) References Cited

U.S. PATENT DOCUMENTS

| 4,033,817 A |   | 7/1977  | Gregor |
| 4,163,714 A |   | 8/1979  | Gregor |
| 4,171,412 A |   | 10/1979 | Coupek et al. |
| 4,639,513 A |   | 1/1987  | Hou et al. |
| 5,071,880 A | * | 12/1991 | Sugo et al. ........................ 521/27 |
| 5,168,041 A | * | 12/1992 | Bergmann ...................... 435/7.1 |
| 5,475,097 A | * | 12/1995 | Travis et al. .................. 536/23.2 |
| 6,248,238 B1 |   | 6/2001  | Burtin et al. |
| 7,067,272 B2 | * | 6/2006  | Nemori et al. .................. 435/23 |
| 2001/0021413 A1 |   | 9/2001 | Tarbet et al. |

FOREIGN PATENT DOCUMENTS

| DE |       44 32 628 A1 |   | 3/1996 |
| WO |       WO 96/40737 |   | 12/1996 |
| WO |       WO 0171025 A1 | * | 9/2001 |
| WO |       WO 02/060952 A1 |   | 8/2002 |

OTHER PUBLICATIONS

Grano, V et al. The alpha1-antitrypsin/elastase complex as an experimental model for hemodialysis in acute catabolic renal failure, extracorporeal blood circulation and cardiocirculatory bypass. International Journal of Artificial Organs. 2002. 25(4): 297-305.*
Pubmed citation of Grano V et al. The alpha1-antitrypsin/elastase complex as an experimental model for hemodialysis in acute catabolic renal failure, extracorporeal blood circulation and cardiocirculatory bypass. Int. J. Artif. Organs. Apr. 2002. 25(4): 297-305. Accessed May 4, 2007.*
Charcosset, C. Purification of proteins by membrane chromatography. J. Chem. Technol. Biotechnol. 1998. 71: 95-110.*
http://www.sigmaaldrich.com/catalog/ProductDetail.do?N4=P5318|SIGMA&N5=SEARCH_CONCAT_PNO|BRAND_KEY&F=SPEC#test. Accessed Sep. 3, 2009.*
http://www.sigmaaldrich.com/catalog/ProductDetail.do?N4=B8385|SIGMA&N5=SEARCH_CONCAT_PNO|BRAND_KEY&F=SPEC#test. Accessed Sep. 9, 2009.*
http://www.sigmaaldrich.com/catalog/ProductDetail.do?lang=en&N4=I9759|SIGMA&N5=SEARCH_CONCAT_PNO|BRAND_KEY&F=SPEC. Accessed Sep. 9, 2009.*
http://www.sigmaaldrich.com/catalog/ProductDetail.do?N4=A6191|SIGMA&N5=SEARCH_CONCAT_PNO|BRAND_KEY&F=SPEC#test. Accessed Sep. 9, 2009.*
http://www.sigmaaldrich.com/catalog/ProductDetail.do?N4=C7268|SIGMA&N5=SEARCH_CONCAT_PNO|BRAND_KEY&F=SPEC#test. Accessed Sep. 9, 2009.*
http://www.sigmaaldrich.com/catalog/ProductDetail.do?N4=L8511|SIGMA&N5=SEARCH_CONCAT_PNO|BRAND_KEY&F=SPEC#test. Accessed Sep. 3, 2009.*
http://www.sigmaaldrich.com/catalog/ProductDetail.do?N4=E3132|SIGMA&N5=SEARCH_CONCAT_PNO|BRAND_KEY&F=SPEC#test. Accessed Sep. 3, 2009.*
http://www.sigmaaldrich.com/catalog/ProductDetail.do?N4=T7254|SIGMA&N5=SEARCH_CONCAT_PNO|BRAND|KEY&F=SPEC#test. Accessed Sep. 3, 2009.*
http://www.chemicalbook.com/ProductChemicalPropertiesCB8384368_EN.htm. Accessed Sep. 3, 2009.*
Carey et al. Organische Chemie. 1995. Plenum Publishing Corporation. p. 1390.*
March, J. Advanced Organic Chemistry. 3rd edition. 1985. John Wiley & Sons, Inc. p. 369.*
Zeng, X et al. Trypsin purification by p-aminobenzamidine immobilized on macroporous chitosan membranes. Ind. Eng. Chem. Res. 1998. 37: 159-165.*
Langlotz, P. Surface-modified membranes as a matrix for protein purification. Journal of Chromatography. 1992. 591: 107-113.*
Hermanson, GT et al. Immobilized affinity ligand techniques. 1992. Academic Press, Inc. San Diego, California.*
Preece, G et al. Metalloproteinase-mediated regulation of L-selectin levels on leucocytes. Journal of Biological Chemistry. 1996. 271(20): 11634-11640.*
Database Biosis 'Online! Biosciences Informationservice, Philadelphia, PA, US; Apr. 2002 Grano V. et al: "The alphal-antitrypsin/elastase complex as an experimental model for hemodialysis ri actue catabolic renal fialure, extracorporeal blood circulation and cardiocirculatory bypass" Database accession No. PREV200200383791 XP002256587.
Database Biosis 'Online! Biosciences Informationservice, Philadelphia, PA, US; Jan. 20, 2003 Grano V. et al: "Protease removal by means of antiprotenses immobilized on supports as a potential tool for hemodialysis or extracorporeal blood circulation." Database accession No. PREV200300399216 XP002256588.

* cited by examiner

*Primary Examiner* — A. M. Ford
*Assistant Examiner* — S. E. Fernandez
(74) *Attorney, Agent, or Firm* — Chernoff Vilhauer McClung Stenzel LLP

(57) ABSTRACT

The invention comprises a membrane and device and method for removing proteases from fluids, particularly from biological fluids and pharmaceutical solutions, which uses a microporous membrane body, whereby inhibitors that selectively bind proteases are coupled to the membrane body by chemically activated groups.

2 Claims, 1 Drawing Sheet

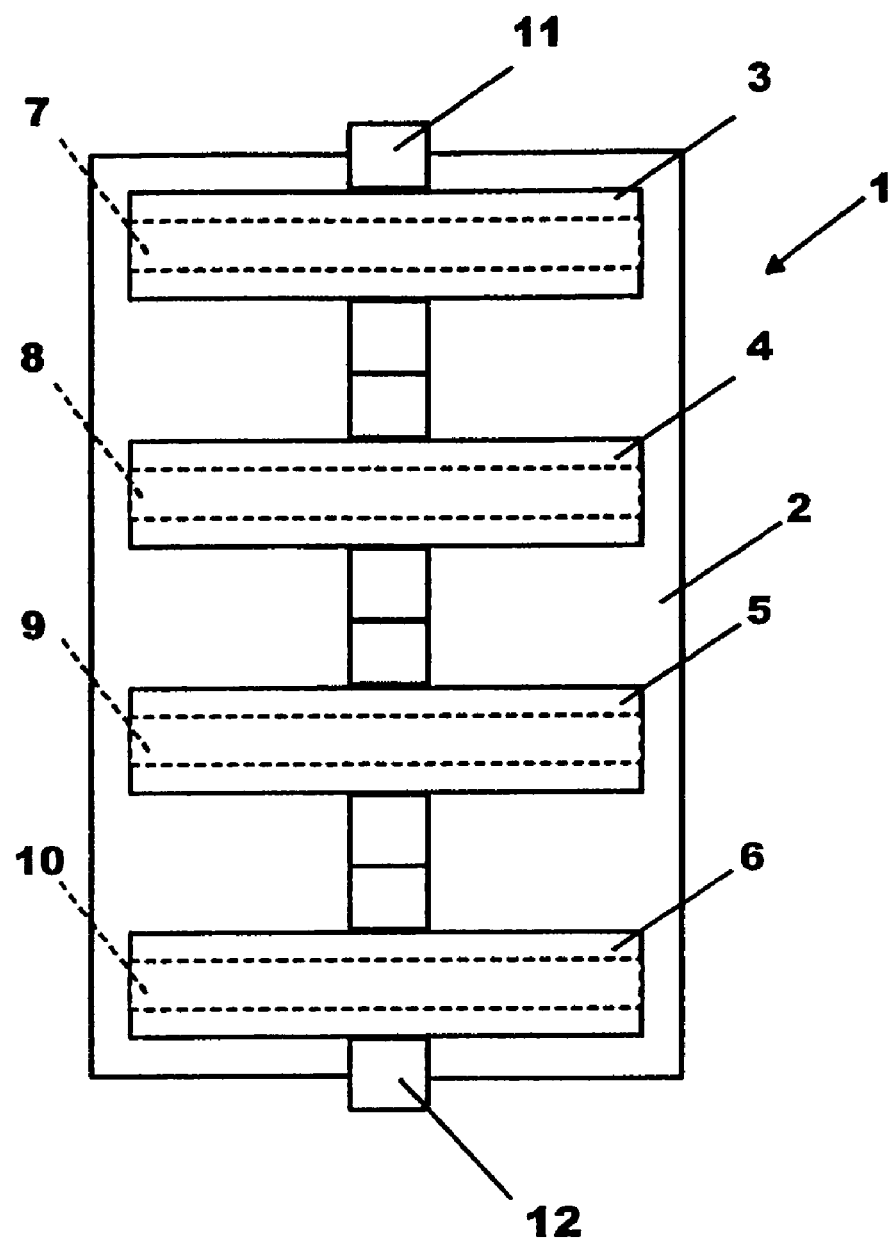

MEMBRANE FOR REMOVING PROTEASES FROM LIQUIDS

This is a divisional of U.S. application Ser. No. 10/516,405 filed Nov. 30, 2004, which in turn is a 371 of PCT/EP2003/006366 filed 17 Jun. 2003 and claiming priority of DE 102 31 574.4 filed 11 Jul. 2002.

BACKGROUND OF THE INVENTION

The stability of pharmaceutical solutions containing proteins is dependent on various factors and especially on the type of pretreatment to which it has been subjected. It is very important that various types of contamination be removed from these solutions, as regulatory authorities require numerous mandatory controls for the removal of contaminants. Contamination with bacteria or fungi can be easily prevented when the pharmaceutical solution is filtered with a sterile ultrafiltration membrane having for instance a nominal pore diameter of 0.2 μm. Viruses can be extracted by a chemical treatment or by the use of a strongly basic ion exchanger. Endotoxins can be also removed with a basic ion exchanger or by ultrafiltration.

Proteases are enzymes which break up proteins and polypeptides by hydrolytically splitting the amino acids which are the building blocks of the proteins. When proteases are present in a pharmaceutical formulation containing a protein such as an antibody, there is a loss of the desired antibody and decomposition products are produced, which cause undesirable side effects in patients who are treated with such a pharmaceutical formulation. During the processing (Down Stream Processing) of a target protein, produced, for example, by gene technology, antibodies can accumulate in the cultured cells and must be separated before further processing. Intrinsic cell proteases are also simultaneously released during lysing of the cells, which can immediately break up the target protein.

In order to prevent or at least delay the deleterious effects of proteases, it is known that small synthetic molecules can be employed which have an inhibitory effect and a very high affinity for the active center of the proteases. A disadvantage in this case is the potential danger presented by such synthetic protease inhibitors, as well as their limited solubility and low stability in aqueous media. That is why a quick and efficient distribution of such protease inhibitors in large volumes is complicated. It is also known to those skilled in the art that chromatographic carriers, such as spherical gels, may be used to immobilize protease inhibitors. Since the removal should occur as far as possible "up stream" in the purification sequence in order to keep the production loss low, large diameter chromatographic columns are required for the processing, making such processing costly and labor-intensive.

It is known from U.S. Pat. No. 6,248,238 that a cationic protease inhibitor can be deployed by means of bulk adsorption onto the surface of a semipermeable membrane comprising a negatively-charged polymer. A disadvantage of such a deployment is that the membrane used is not electrically neutral, but instead, is negatively charged with the monomer used, often causing irreversible binding.

DE 44 32 628 A1 discloses a dead-end filtration module for the selective separation of substances from fluids by filtration on porous membrane adsorbers. The individual substances to be separated are retained on the filter cassettes or membranes in accordance with a specific adsorption provided by ion exchange or by membranes carrying pigment ligands. The adsorbed substances are selectively desorbed, eluted and absorbed with suitable elution fluids. However, it is difficult to bind all classes of known proteases to such membrane adsorbers.

Accordingly, the principal object of the present invention is to provide membranes for the quick, efficient and inexpensive removal of a broad spectrum of proteases including acid proteases, metalloproteases, cystein proteases and serine proteases from biological fluids and pharmaceutical liquids so that their deleterious effects may be prevented or at least delayed.

BRIEF SUMMARY OF THE INVENTION

The foregoing object is achieved by chemically activating the surfaces of membranes with functional groups that in turn are coupled with inhibitors capable of selectively binding proteases.

There are three aspects to the present invention: (1) a microporous chemically activated adsorber membrane containing coupled affinity ligands for removing proteases from biological fluids and pharmaceutical solutions; (2) a device for removing proteases from biological fluids and pharmaceutical solutions, comprising a plurality of the membranes described in (1) connected in series; and (3) a method for removing proteases from biological fluids and pharmaceutical solutions by microfiltration with the membranes described in (1).

BRIEF DESCRIPTION OF THE DRAWINGS

FIG. 1 is a schematic of an exemplary device of the invention for removing proteases.

DETAILED DESCRIPTION OF PREFERRED EMBODIMENTS

The advantage of the use of the membranes of the invention is that a higher convective flow through such membranes is achieved in comparison to corresponding columns, because for all practical purposes the diffusion limitation of the mass transport is negligible. The amount of inhibitor coupled to the membrane and the membrane's surface area can be adjusted, depending on the amount of the proteases to be removed. The membrane can be discarded after it has been used, which saves on purification and validation costs.

The present invention is capable of removing a broad spectrum of proteases. Acid proteases, which have an aspartic acid radical in the active center, can be adsorbed with a suitable inhibitor coupled to the membrane, e.g., pepstatin, which efficiently inhibits the protease pepsin. Metalloproteases, which have a transition metal such as zinc in the active center, can be adsorbed for example with bestatin, diprotin or EDTA, any of which may be coupled to the membrane. Cystein proteases, which have a cysteine radical in the active center, e.g., papain from papaya, can be adsorbed with antipain, chymostatin or N-[N-(L-3-trans-carboxyoxiran-2-carbonyl) L-leucyl]-agmatin (E 64), any of which may be coupled to the membrane. Serine proteases, which due to their ubiquitous presence are the most important family, can be bound with suitable inhibitors coupled to the membrane, such as L-1-chloro-3-(4-tosylamido)-7-amino-2-heptanone-hydrochloride (TLCK) and p-aminobenzamidine. For cysteine proteases and serine proteases there are also large molecule inhibitors of the protein type such as aprotinine, soy bean inhibitors, trypsine inhibitors and alpha-2-macroglobulin. All of the inhibitors mentioned above are small molecules, often peptide-type or peptide analogs, and all of them are commercially available. A large number of other inhibitors are described in the literature, all of which can be used in accordance with the invention.

The protease removal device of the invention comprises a plurality of the adsorber membranes described above arranged in series, which guarantees that the fluids to be processed will flow sequentially through the first and all successive adsorber membranes. The membranes can be adjusted in a relatively simple manner according to respective separation problems.

In a preferred embodiment of the invention, the individual adsorber membranes are provided with a membrane body that is coupled to one or more other inhibitors, making it possible to take into account the relevant protease spectrum of different fluids to be processed. To achieve simple handling, individual membranes are incorporated into a suitable housing designed for sequential through-flow.

The protease removal method of the present invention comprises simply contacting the adsorber membrane(s) described above with the biological fluid or pharmaceutical composition containing proteases, thereby permitting the proteases to be adsorbed onto the membrane(s) and so removed through selective binding.

Referring to FIG. 1, there is shown an exemplary device 1 for removing proteases, essentially comprising a housing 2 and four microporous membranes 3, 4, 5 and 6 arranged in series. The first membrane 3 is provided with a first membrane body 7, to which an inhibitor that binds acidic proteases is coupled by a chemically activated or functional group; pepstatin would be a suitable inhibitor. The second membrane 4 is provided with a second membrane body 8, to which an inhibitor that binds metalloproteases is coupled by a chemically activated group; exemplary suitable inhibitors include bestatin, diprotin and EDTA. The third membrane 5 is equipped with a third membrane body 9, to which an inhibitor that binds cysteine proteases is coupled by a chemically activated group; exemplary suitable inhibitors include antipain, chymostatin and E 64. The fourth membrane 6 is equipped with a fourth membrane body 10, to which an inhibitor that binds serine proteases is coupled by a chemically activated group; exemplary suitable inhibitors include TLCK and p-aminobenzamidine.

The fluid to be processed is supplied to the first membrane 3 by a fluid inlet connection 11 arranged in the housing 2, whereby the corresponding acidic proteases will bind to the inhibitor of the first membrane body 7. The fluid to be processed next contacts the second membrane 4, whereby the corresponding metalloproteases will be bound to the inhibitor of the second membrane body 8. The fluid next contacts the third membrane 5, whereby corresponding cysteine proteases will bind to the inhibitor of the third membrane body 9. Finally, the fluid contacts the fourth membrane 4, whereby the corresponding serine proteases will bind to the inhibitor of the fourth membrane body 10.

The protease removal preferably takes place at a point that is remote from the finally processed fluid, so that the proteases can be later recovered if desired by elution through discharge channel 12. Alternatively, membranes 3, 4, 5 and 6 may be discarded along with the bound proteases.

The following Examples show the possibilities for binding different protease inhibitors to a chemically activated membrane or membrane body. The procedures for both Examples were carried out substantially according to the protocol described in G. T. Hermanson et al., *Immobilized Affinity Ligand Techniques*, p. 119 (1992).

Example 1

The serine protease inhibitor p-aminobenzamidine (Sigma, Deisonhofen Order No. A-7148), was dissolved in 0.05 M potassium phosphate buffer, pH 8.0, at a concentration of 20 mg/mL. Ten 25 mm-diameter regenerated cellulose functionalized (epoxy-activated) microporous membranes (Sartobind® epoxy from Sartorius AG of Göttingen, Germany) were incubated overnight in the protease inhibitor-containing phosphate buffered solution at 45° C. to chemically couple the serine protease inhibitor to the membranes via the membranes' epoxy functional groups. The membranes/membrane bodies were rinsed several times with a phosphate buffered saline (PBS) solution. Three of the 10 membranes were inserted in series into a filter holder (Sartorius Part No. 16517). The serine protease trypsine from bovine pancreas (Sigma, Order No. T-8003, Lot No. 28F-8065) was dissolved in PBS at a concentration of 1 mg/mL. Ten mL of this solution was then gravity filtered through the three membranes, followed by rinsing them with 10 mL of PBS. The bound trypsine was adjusted with 3 mL of 0.1 M glycine and eluted to pH 3.0 with HCl. The enzymatic activity of the trypsine in various fractions was determined with the synthetic substrate benzoyl arginine ethyl ester (BAEE), a known substrate for trypsine, in a UV spectrophotometer. These activities were then compared to the activities of control trypsine solutions whose trypsine concentrations were known.

The following items were transferred with a pipette into a quartz cuvette: 0.85 mL of a 0.85 M Tris solution adjusted with HCL to pH 8.5; 0.2 mL of a solution of 2 mg/mL BAEE in water; and 0.05 mL of the sample. The increase of absorption at 253 nm took place over a period of 30 seconds. The resulting binding of trypsine to the epoxy-functionalized and protease inhibitor-coupled membranes is listed in Table 1.

TABLE 1

| Fraction | Volume (mL) | Activity (E253/min) | µg of Trypsin Supplied | µg of Trypsin Bound |
|---|---|---|---|---|
| Initial Capacity | 10 | 0.24 | 2000 | — |
| Through Flow | 10 | 0.144 | | 930 |

The test was repeated twice with the same result, and clearly demonstrates binding of trypsine to the membrane/membrane bodies charged with the serine protease inhibitor.

Example 2

The cysteine protease inhibitor leupeptin (Sigma, Deisenhofen, Order No. L-2033) was dissolved in a 0.05 M potassium phosphate buffer, pH 8.0, at a concentration of 20 mg/mL. Ten epoxy-activated membranes/membrane bodies of the type used in Example 1 were incubated overnight in this solution at 45° C. to chemically couple the cysteine protease inhibitor to the membranes via the membranes' epoxy functional groups. The membranes were rinsed several times with PBS. Three of the 10 membranes were inserted into the same type of filter holder used in Example 1, the cysteine protease papain from Carica papaya (Merck Art. No. 7144 Ch. 9I1 F739244, 30 000 USP—U/mg) was dissolved at a concentration of 2 mg/ml in the following four-component buffer: 1.1 mM EDTA, 0.67 mM mercaptoethanol, 5.5 mM cysteine and 50 mM Na-acetate, pH 5.5 and allowed to react for at least 30 minutes at room temperature. The enzymatic activity of papain in the various fractions was determined with the synthetic substrate benzoyl-arginine-nitroanilide (BANA), a known substrate for papain, in a UV spectrometer. This activity was compared to activities of papain control solutions with different known papain concentrations.

The following items were transferred with a pipette into a quartz cuvette: 0.5 mL of an enzyme solution, 0.05 mL of 25 mg/mL BANA in DMSO; and 0.45 mL of the above four-component buffer.

The resulting binding of papain to the functionalized membranes is listed in Table 2.

TABLE 2

| Fraction | Volume (mL) | Activity (E253/min) | µg of Trypsin Supplied | µg of Trypsin Bound |
|---|---|---|---|---|
| Initial Capacity | 5 | 0.05 | 1900 | — |
| Through Flow | 5 | 0.03 | | 760 |

The test was repeated twice with the same result and clearly demonstrates binding of papain to the membrane/membrane bodies charged with the inhibitor.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

The invention claimed is:

1. A membrane for removing proteases from a fluid, consisting essentially of an epoxy-functionalized microporous membrane containing epoxy groups chemically coupled to at least one protease inhibitor selected from the group consisting of pepstatin, bestatin, diprotin, antipain, chymostatin, leupeptin, E64, TLCK and p-aminobenzamidine, wherein said at least one protease inhibitor is coupled by a chemical bond to said membrane via said epoxy groups.

2. The membrane of claim 1 wherein said microporous membrane contains two different protease inhibitors.

* * * * *